(12) United States Patent
Lin

(10) Patent No.: US 10,926,055 B2
(45) Date of Patent: Feb. 23, 2021

(54) HEALTHY GAS GENERATING SYSTEM

(71) Applicant: Hsin-Yung Lin, Shanghai (CN)

(72) Inventor: Hsin-Yung Lin, Shanghai (CN)

(*) Notice: Subject to any disclaimer, the term of this patent is extended or adjusted under 35 U.S.C. 154(b) by 411 days.

(21) Appl. No.: 15/662,129

(22) Filed: Jul. 27, 2017

(65) Prior Publication Data

US 2018/0028774 A1 Feb. 1, 2018

(30) Foreign Application Priority Data

Jul. 27, 2016 (TW) .............................. 105211325 U

(51) Int. Cl.

| | | |
|---|---|---|
| A61M 16/12 | (2006.01) | |
| A61M 16/00 | (2006.01) | |
| C25B 1/04 | (2006.01) | |
| C25B 15/02 | (2006.01) | |
| B01D 53/78 | (2006.01) | |
| B01D 53/68 | (2006.01) | |
| B01D 53/14 | (2006.01) | |
| B01D 53/18 | (2006.01) | |

(52) U.S. Cl.
CPC ........ *A61M 16/12* (2013.01); *A61M 16/0087* (2013.01); *B01D 53/1493* (2013.01); *B01D 53/18* (2013.01); *B01D 53/68* (2013.01); *C25B 1/04* (2013.01); *C25B 15/02* (2013.01); *A61M 2202/02* (2013.01); *A61M 2207/00* (2013.01); *B01D 53/78* (2013.01); *B01D 2252/103* (2013.01); *B01D 2256/16* (2013.01); *B01D 2257/2025* (2013.01); *B01D 2259/4533* (2013.01); *Y02E 60/36* (2013.01)

(58) Field of Classification Search
CPC ...... A61M 2202/02; A61M 2202/0007; A61M 16/0087; A61M 16/12; A61M 2207/00; A61M 16/00; A61M 16/122; B01D 2252/103; B01D 2256/16; B01D 2257/2025; B01D 2259/4533; B01D 53/1493; B01D 53/18; B01D 53/68; B01D 53/78; C25B 15/02; C25B 1/04; Y02E 60/366
See application file for complete search history.

(56) References Cited

U.S. PATENT DOCUMENTS

| | | | | |
|---|---|---|---|---|
| 3,917,520 | A * | 11/1975 | Katz | .......................... C25B 1/04 205/349 |
| 4,436,793 | A * | 3/1984 | Adlhart | ................. H01M 8/065 429/421 |
| 6,351,982 | B1 * | 3/2002 | Tindall | ..................... G01N 27/16 264/35 |
| 8,449,737 | B2 * | 5/2013 | Richardson | ............... C25B 1/04 204/268 |

(Continued)

*Primary Examiner* — Michael J Tsai
*Assistant Examiner* — Nathan M Le
(74) *Attorney, Agent, or Firm* — Foster Garvey PC

(57) ABSTRACT

A healthy gas generating system for generating healthy gas for inhalation by a user includes an electrolysis device, a gas mixing device, and a backfire barrier. The electrolysis device electrolyzes water to generate a gas with hydrogen. The gas mixing device includes a mixer and a vibrator for mixing the combination gas with an atomized gas to produce the healthy gas. The backfire barrier is configured on the output of the gas mixing device or the gas passage of receiving the combination gas to avoid the backflow of the gas.

11 Claims, 5 Drawing Sheets

(56) References Cited

U.S. PATENT DOCUMENTS

| | | | | |
|---|---|---|---|---|
| 2004/0146759 A1* | 7/2004 | Hecker | | B01D 53/326 |
| | | | | 205/343 |
| 2007/0012264 A1* | 1/2007 | Holt | | C25B 1/06 |
| | | | | 123/1 A |
| 2009/0281480 A1* | 11/2009 | Orlebeke | | A01K 63/042 |
| | | | | 604/24 |
| 2010/0155233 A1* | 6/2010 | Hwang | | C25B 1/04 |
| | | | | 204/228.6 |
| 2010/0187128 A1* | 7/2010 | Neubert | | B01D 1/22 |
| | | | | 205/743 |
| 2011/0057455 A1* | 3/2011 | Russo | | C25B 1/04 |
| | | | | 290/1 A |
| 2011/0247620 A1* | 10/2011 | Armstrong | | B01D 53/047 |
| | | | | 128/204.23 |
| 2011/0303194 A1* | 12/2011 | Fong | | F02D 19/081 |
| | | | | 123/486 |
| 2012/0067021 A1* | 3/2012 | Aggelopoulos | | C25B 1/08 |
| | | | | 60/39.12 |
| 2013/0092558 A1* | 4/2013 | Kim | | C02F 1/4618 |
| | | | | 205/743 |
| 2013/0133650 A1* | 5/2013 | Zhao | | A61P 31/06 |
| | | | | 128/203.12 |
| 2013/0206586 A1* | 8/2013 | Lin | | C25B 15/02 |
| | | | | 204/228.2 |
| 2014/0048067 A1* | 2/2014 | McGill | | A61M 16/10 |
| | | | | 128/203.29 |
| 2014/0352689 A1* | 12/2014 | Seshadri | | A61M 15/0085 |
| | | | | 128/200.16 |
| 2014/0374243 A1* | 12/2014 | Lin | | A61M 16/125 |
| | | | | 204/228.3 |
| 2015/0124920 A1* | 5/2015 | Kawamura | | G21B 3/00 |
| | | | | 376/100 |
| 2015/0144483 A1* | 5/2015 | Lin | | C25B 15/02 |
| | | | | 204/274 |
| 2015/0258298 A1* | 9/2015 | Satoh | | A61K 33/00 |
| | | | | 128/202.26 |
| 2016/0199603 A1* | 7/2016 | Kawamura | | A61M 16/0891 |
| | | | | 128/200.19 |
| 2016/0263341 A1* | 9/2016 | Lin | | C25B 15/02 |

\* cited by examiner

HEALTHY GAS GENERATING SYSTEM

BACKGROUND OF THE INVENTION

Field of the Invention

The present invention relates to a healthy gas generating system, more particularly, to a healthy gas generating system for producing healthy gas with hydrogen and for preventing explosion.

Description of the Prior Art

As people have always been paying much attention on health developments, many developments in medical technology are often targeted on treating diseases and prolonging human life. Also, most of the treatments in the past are passive, which means that the disease is treated only when it occurs, and the treatments may include an operation, a medication treatment, a radiation therapy, or a medical treatment for cancer. However, in recent years, most of the medical experts' researches are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and are becoming increasingly popular to the general public.

Studies have found that there are instable oxygen species ($O^+$), also known as free radicals, in the human body. The free radicals are usually generated due to diseases, diet, and environment. And, one's lifestyle can be excreted in the form of water by reacting with the inhaled hydrogen. With this method, the amount of free radicals in the human body can be reduced, thereby restoring the body condition from an acidic state to an alkaline state, to achieve an anti-oxidation, anti-aging and beauty health effect, and even to eliminate chronic diseases. Furthermore, there are also clinical experiments showing that patients who need to inhale a high concentration of oxygen for an extended period of time would experience lung damage. However, it could be ameliorated by inhaling hydrogen. As the human tracheal structure is unsuitable for inhaling dry gas, the hydrogen must be properly humidified before the patient inhales.

In addition to being used in hospitals or other medical units, the use of humidified hydrogen at home can further achieve the effect of early prevention of the disease. In the prior art, the household hydrogen generation machine can not only generate humidified hydrogen, but also can mix the humidified hydrogen and a variety of atomized liquid to generate the health gas to get better results. According to different atomized liquid, there may be an optimally healthy gas volume proportion of hydrogen to atomized gas in different treatments. However, if the hydrogen ratio exceeds a certain degree, it may cause an explosion to damage the entire hydrogen generation machine. Therefore, it is necessary to design a new type of hydrogen generation machine for generating the hydrogen-containing health gas and preventing the damage of the machine from explosion.

SUMMARY OF THE INVENTION

Therefore, the present inventor with many years engaged in the manufacture and development of related products and design experience went through the detailed design and careful assessment to finally confirm that the present invention is practically usable.

A primary object of the present invention is to provide a healthy gas generating system. The system generates healthy gas with hydrogen for inhalation by a user, and further prevents the damage of the healthy gas generating system from an explosion.

According to one embodiment of the present invention, the healthy gas generating system comprises an electrolysis device, a gas mixing device, and a backfire barrier. The electrolysis device electrolyzes water to generate a gas with hydrogen. The gas mixing device further comprises a gas mixing tank, having a shell, wherein the shell further comprises a first communication port connected to the electrolysis device and a first gas outlet. The gas mixing tank receives the gas with hydrogen via the first communication port, and the gas mixing tank mixes the gas with hydrogen with an atomized gas to generate a healthy gas and outputs the healthy gas via the first gas outlet. The backfire barrier is configured on the shell at either the first gas outlet or the first communication port to avoid backflow of the gas.

According to another embodiment of the present invention, the backfire barrier is an anti-backfire device. In an embodiment, in the event of an accident or system instability, the fire of the explosion or burning point will spread through the passage to the source of the gas, called backfire, and the anti-backfire device is used to prevent the fire from flowing back to the gas source. Since the backfire barrier is configured in the gas passage, even if the proportion of the hydrogen gas discharged from the output gas is too high, the backfire barrier will prevent the fire from flowing back to the healthy gas generating system. Therefore, the anti-backfire device can prevent the damage to the system from an explosion.

According to another embodiment of the present invention, the volume ratio of the hydrogen in the healthy gas generated by the system above mentioned is less than 2%.

According to another embodiment of the present invention, the volume ratio of the hydrogen in the healthy gas generated by the system above mentioned is between 2% to 96%.

According to another embodiment of the present invention, the volume ratio of the hydrogen in the healthy gas generated by the system above mentioned is over 96%.

According to another embodiment of the present invention, the gas mixing device of the above mentioned further comprises a humidifier coupled to the electrolysis device and the gas mixing tank, and the humidifier receives and filters the gas with hydrogen. The gas mixing tank mixes the filtered gas with an atomized gas to generate a healthy gas with hydrogen.

According to another embodiment of the present invention, the healthy gas generating system further comprises a diversion valve configured between the humidifier and the gas mixing tank. The diversion valve can be selectively connected to the humidifier and the gas mixing tank, so that the filtered gas with hydrogen is selectively mixed with the atomized gas to generate the healthy gas or output directly.

According to another embodiment of the present invention, the backfire barrier is formed with the shell by the method of injection molding, for allowing the backfire barrier and the shell to be formed in one piece. The backfire barrier is configured on the shell at either the first gas outlet or the first communication port to avoid the backflow of the gas.

According to another embodiment of the present invention, the shell of the gas mixing tank accommodates a shock base liquid, and the gas mixing tank comprises a mixing cup and a vibrator. The mixing cup is configured in the shell and partially soaked in the shock base liquid. The mixing cup further comprises a second communication port and a second gas outlet. The second communication port is connected between the humidifier and the first communication port. The second gas outlet is connected to the first gas outlet, and the mixing cup accommodates a liquid, wherein the liquid comprises at least one of essential oil, syrup and pure water. The vibrator is configured on the shell, wherein the vibrator shakes the liquid in the mixing cup via the shock base liquid to generate the atomized gas.

According to another embodiment of the present invention, the gas mixing device selectively outputs the gas by the user's selection of turning on or off the vibrator.

According to another embodiment of the present invention, the healthy gas generating system further comprises a flow controller, wherein the flow controller is coupled to the electrolysis device to detect a flow rate of the gas with hydrogen, and the detected flow rate controls the production of the gas with hydrogen in the electrolysis device.

According to another embodiment of the present invention, the flow controller selectively cuts an input voltage or an input current of the electrolysis device according to the flow rate.

According to another embodiment of the present invention, the healthy gas generating system further comprises an adding gas unit. The adding gas unit is configured between the electrolysis device and the gas mixing device for adding a gas into the gas with hydrogen to reduce the volume ratio of the hydrogen, wherein the gas comprises at least one of air, water vapor, blunt gas and oxygen.

According to another embodiment of the present invention, the electrolysis device comprises two electrodes electrically connected to a power supply, and the output voltage of the power supply is less than 24V.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
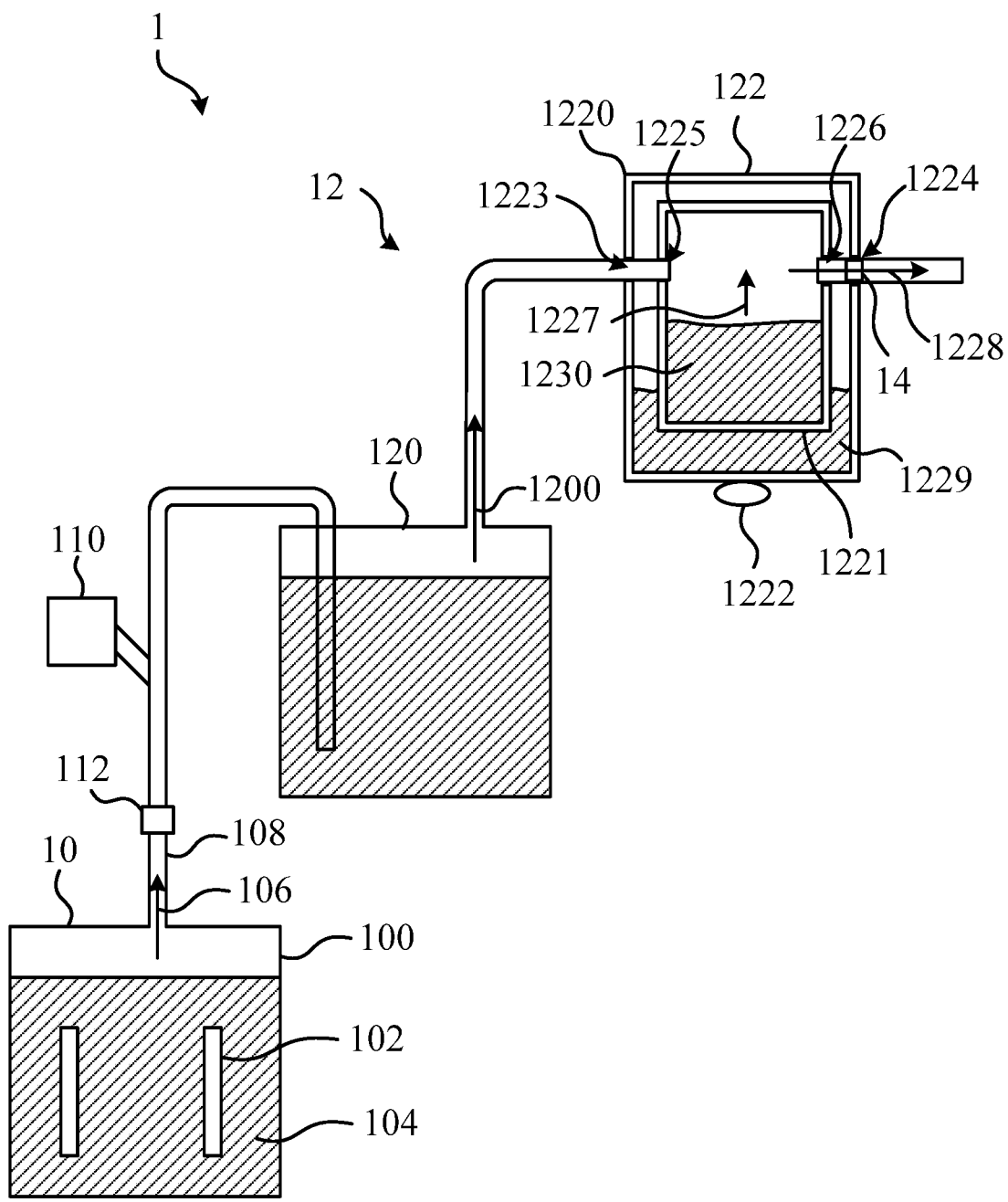
FIG. 1 shows a schematic diagram of the healthy gas generating system in one embodiment of the present invention.

Please refer to FIG. 1. FIG. 1 shows a schematic diagram of the healthy gas generating system 1 in one embodiment of the present invention. The healthy gas generating system 1 comprises an electrolysis device 10, a gas mixing device 12, and a backfire barrier 14, wherein the electrolysis device 10 is connected to the gas mixing device 12.

The electrolysis device 10 comprises an electrolysis tank 100 and at least two electrodes 102 configured inside the electrolysis tank 100. The electrolysis tank 100 accommodates an electrolyzed water 104. The main component of the electrolyzed water 104 is pure water; if necessary, an additional small amount of electrolyte, such as sodium hydroxide, calcium carbonate, or sodium chloride, can be added. The anode and cathode of the two electrodes 102 are respectively connected to the positive and negative electrodes 102 of a power supply (not shown) for providing the electrical energy required for electrolyzed water. In one embodiment, the polarity of the two electrodes 102 may be fixed, such as the left electrode 102 fixed to the cathode and the right electrode 102 fixed to the anode. However, in other embodiments, the polarity of the two electrodes 102 may be alternately transformed. For example, at some point in time, the left electrode 102 is the cathode and the right electrode 102 is the anode; at another point, the left electrode 102 is switched to the anode and the right electrode 102 is switched to the cathode. Although certain embodiments are shown and described in detail, it should be understood that various changes and modifications may be made without departing from the scope of the appended claims. The two electrodes 102 of the electrolysis device are not limited to the form of the above-described embodiment, and any combination of electrodes 102 capable of electrolyzing water for producing gas with hydrogen are alternatives to the present invention. For example, one of the electrodes 102 of the electrolysis device may be a sheet or rod-like electrode located in the center of the electrolysis tank while the other electrode may be the inner wall of the electrolysis tank. In another embodiment, the output voltage supplied by the power supply may be less than 24V, and the probability of damage to the capacitance in the circuit of the healthy gas generation system 1 may be reduced.

The electrolyzed water 104 in the electrolysis tank 100 is electrolyzed by the electrode 102 to respectively generate hydrogen gas and oxygen gas at the electrodes 102 of different polarities. The both gases are raised to the upper portion of the electrolysis tank 100 to form the gas with hydrogen 106 and are passed through the output passage 108. In another embodiment, the oxygen produced by the cathode and the oxygen produced by the anode may be led out of the electrolysis tank 100 by a different gas conduit, followed by mixing to produce a hydrogen-oxygen mixed gas. The ratio of hydrogen to oxygen is about 2:1. In one embodiment, there is an adding gas unit 110 configured on the output passage 108 for adding additional gas to the gas with hydrogen 106 in order to reduce the concentration of hydrogen. The added gas may be air, blunt (such as nitrogen, etc.), oxygen, water vapor, or any combination of the above gases. It should be understand that the adding gas unit 110 reduces the concentration of hydrogen in the gas with hydrogen 106 first and then stabilizes the gas with hydrogen 106 when the gas with hydrogen 106 is conveyed. However, this feature does not represent the hydrogen concentration of the finally produced healthy gas is the same as the gas with hydrogen 106.

In one embodiment, a flow controller 112 is configured in the output passage 108 for detecting the flow rate of the gas with hydrogen 106 and to adjust the magnitude (power) of the voltage or current applied to the electrode 102 in accordance with the flow rate to control the gas production amount. In addition to adjusting the magnitude of the voltage or current of the electrode 102, the flow controller 112 may directly cut off the voltage or current applied to the electrode 102 when the flow controller 112 detects an abnormal value. It is noted that the above-mentioned adding gas unit 110 and the flow controller 112 are selectively used, that is, they can be used at the same time, alternatively, or not used at all, or even by other devices with similar functions. In some embodiments, the electrolysis tank 100 may comprise an input line, and the electrolyzed water 104 in the electrolytic tank 100 may be replenished by the input line.

The gas mixing device 12 is coupled to the electrolysis device 10, i.e. the output passage 108 is connected to the gas mixing device 12 so that the gas mixing device 12 can receive the gas with hydrogen 106. The gas mixing device 12 may comprise a gas mixing tank 122 which includes a shell 1220, and the shell 1220 is connected to the electrolysis device 10. Besides, the gas mixing tank 122 further comprises a mixing cup 1221 and a vibrator 1222, wherein the mixing cup 1221 is configured in the shell 1220, and the vibrator 1222 is configured on the shell 1220. The shell 1220 comprises a first communication port 1223 and a first gas outlet 1224, and the mixing cup 1221 comprises a second communication port 1225 and a second gas outlet 1226. The first communication port 1223 and the second communication port 1225 are connected to the electrolysis device 10, and the first gas outlet 1224 communicates with the second gas outlet 1226. The first communication port 1223 and the second communication port 1225 are connected to the electrolysis device 10, and the first gas outlet 1224 communicates with the second gas outlet 1226.

The gas mixing device 12 may further comprises a humidifier 120 connected between the electrolysis device 10 and the gas mixing tank 122; in detail, the humidifier 120 is connected between the output passage 108 of the electrolysis device 10 and the first communication port 1223 of the gas mixing tank 122. The humidifier 120 contains water for filtering gas with hydrogen 106 to produce a filtered gas 1200, wherein the gas with hydrogen 106 is delivered into the humidifier 120 through the output passage 108. In some embodiments, the purpose of the humidifier 120 is to filter other gases, such as chlorine, other than hydrogen and oxygen that may be contained in gas with hydrogen 106 produced by the electrolysis device 10. Thus, the humidifier 120 can accommodate not only water but also any liquid capable of absorbing either gases, except oxygen and hydrogen, or impurities.

The gas mixing tank 122 may receive the filtered gas 1200 from the humidifier 120 through the first communication port 1223 and the second communication port 1225. Then, the filtered gas 1200 is mixed with the atomized gas 1227 to form the healthy gas 1228. The healthy gas 1228 may be outputted from the first gas outlet 1224 and the second gas outlet 1226 to a respirator or the like for inhalation by a user.

The shell 1220 contains a shock base liquid 1229, and the mixing cup 1221 is partially immersed in the shock base liquid 1229. The vibrator 1222 may oscillate the mixing cup 1221 through an ultrasonic shock. Liquid 1230 is accommodated in the mixing cup 1221 and the liquid 1230 can be atomized into the above-described atomized gas 1227. Thus, the healthy gas 1228 is formed through mixing the filtered gas 1200 with the atomized gas 1227. The liquid 1230 may be essential oil, syrup, pure water or a combination thereof so that the generated atomized gas 1227 may be volatile essential oil, aerosolized syrup, atomized water vapor or a combination thereof.

In addition to the device described above, the healthy gas generation system 1 further comprises a backfire barrier 14, which may be disposed over the shell 1220 and located at the first gas outlet 1224. In an embodiment, the backfire barrier 14 is formed with the shell 1220 by method of injection molding, for allowing the backfire barrier 14 and the shell 1220 to be formed in one piece. The backfire barrier 14 may be an anti-backfire device with its function to cause the healthy gas 1228 generated by the gas mixing tank 122 to exit outwardly and to prevent the healthy gas 1228 from flowing back into the gas mixing tank 122. Thus, even in the event of an accident or system instability, regardless of the proportion of the hydrogen in the healthy gas 1228, the fire of the explosion in the healthy gas 1228 will in no way damage the body of the healthy gas generation system 1. Therefore, the anti-backfire device can prevent the damage of the system from the explosion. In addition, since the backfire barrier 14 has an explosion-proof effect, the concentration of hydrogen in the healthy gas 1228 can be alternatively adjusted. For example, the volume ratio of the hydrogen may be 2% or less, between 2% and 96% or more.

Figure 2:
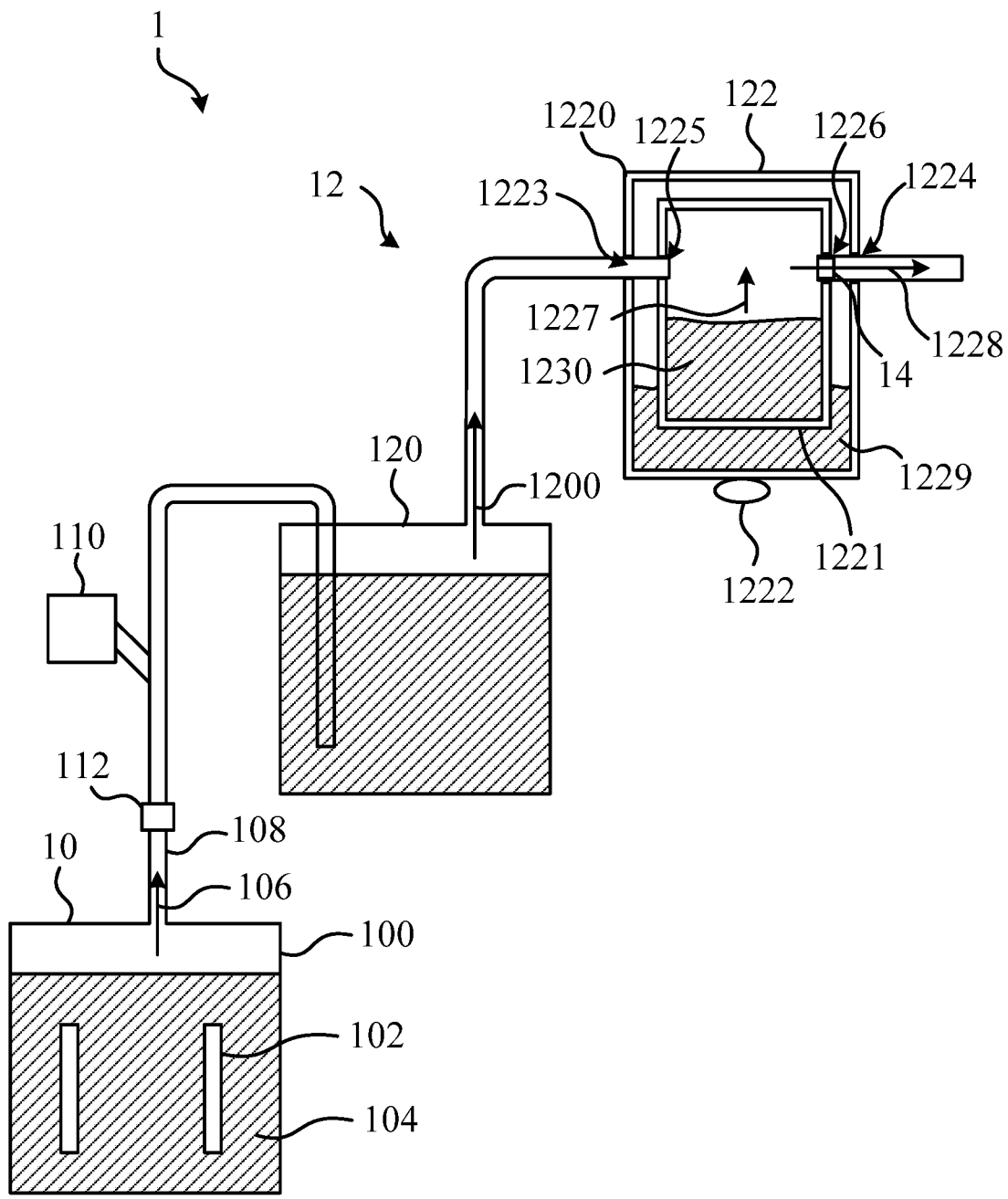
FIG. 2 shows a schematic diagram of the healthy gas generating system in another embodiment of the present invention.
Figure 3:
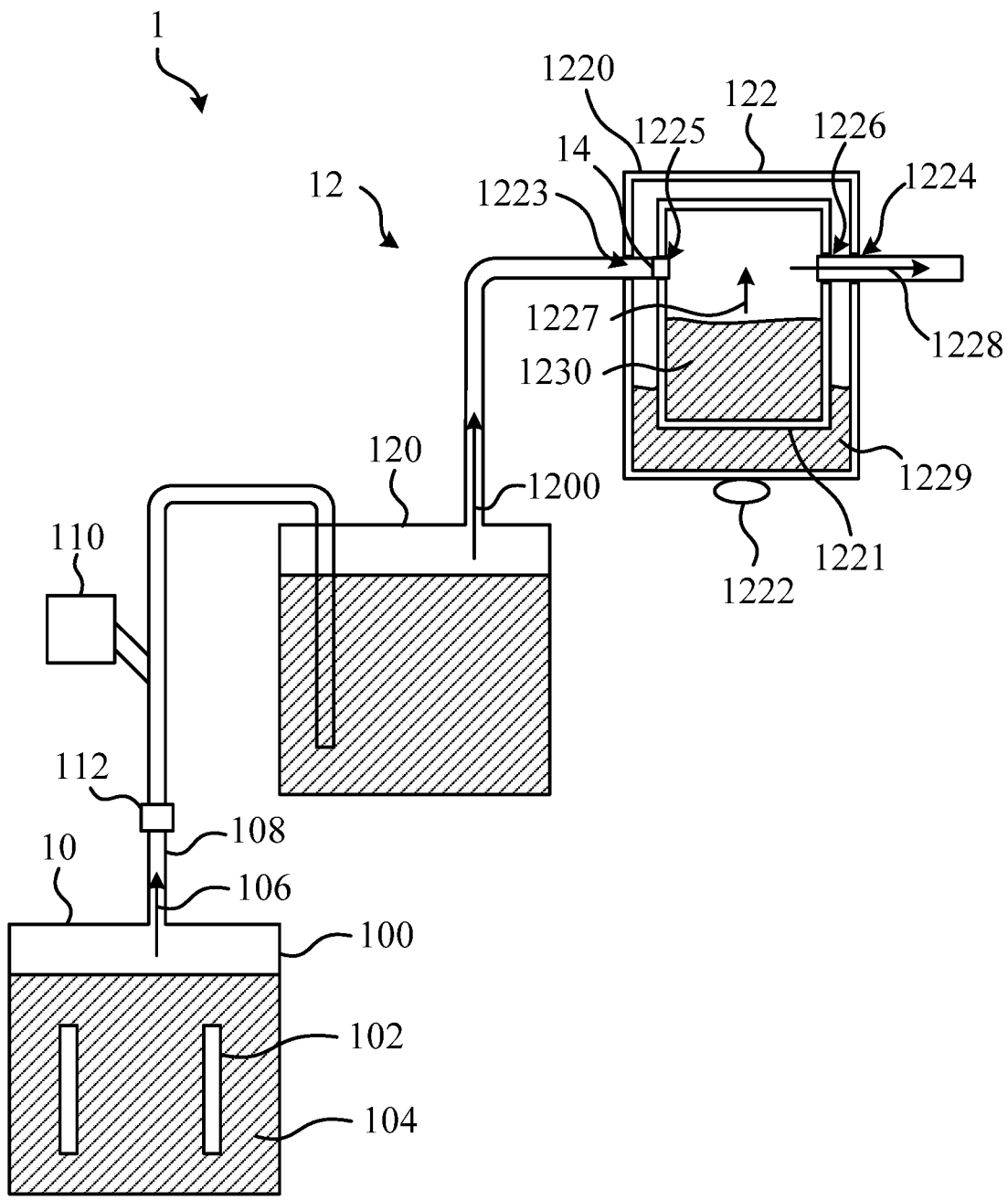
FIG. 3 shows a schematic diagram of the healthy gas generating system in another embodiment of the present invention.
Figure 4:
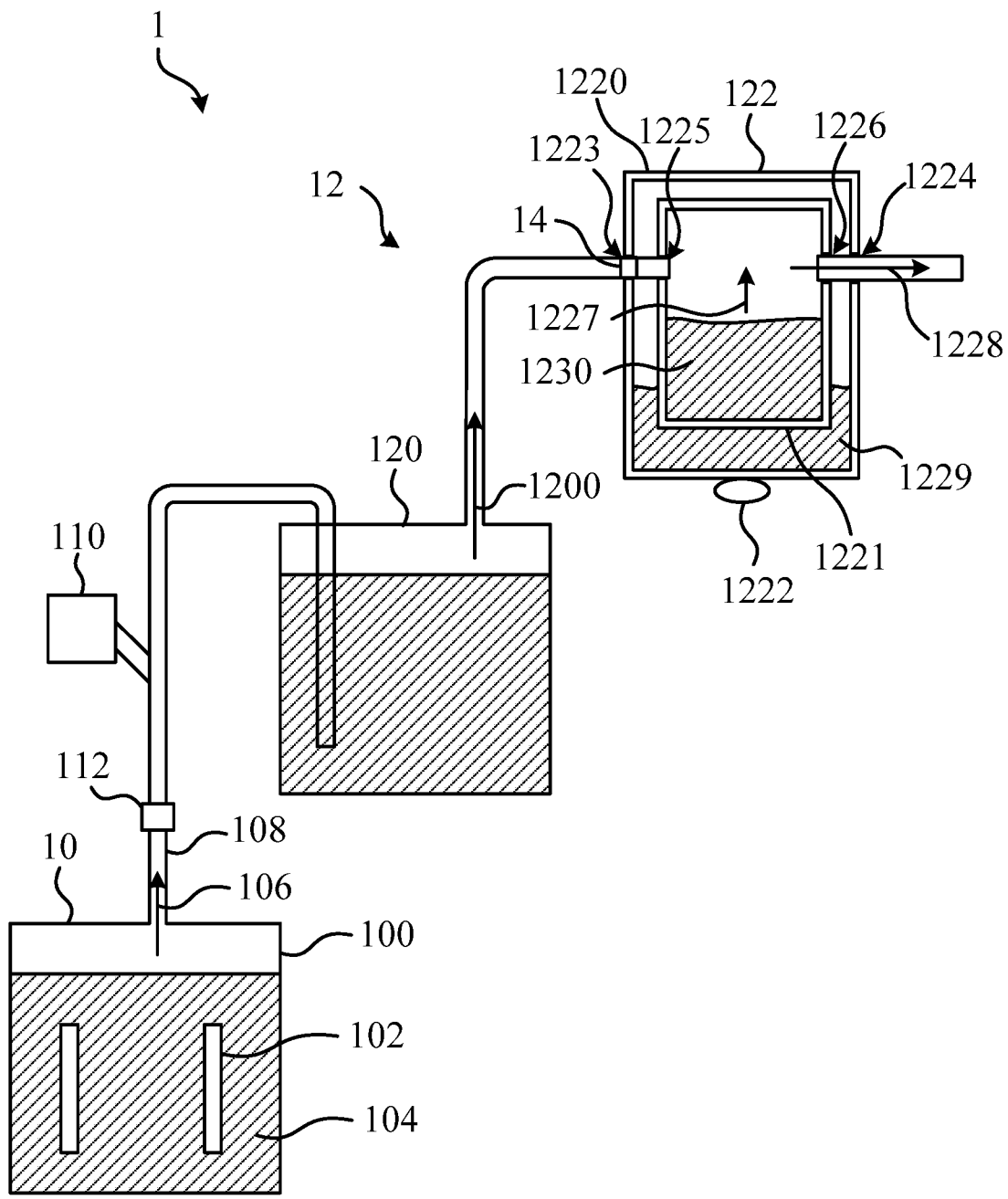
FIG. 4 shows a schematic diagram of the healthy gas generating system in another embodiment of the present invention.

The backfire barrier 14 may be disposed at other locations on the gas passage in addition to the first gas outlet 1224. Please refer to FIG. 2 to FIG. 4. FIG. 2 to FIG. 4 show the schematic diagrams of the healthy gas generating system 1 in other embodiments of the present invention. As shown in FIG. 2 to FIG. 4, the embodiment is different in that the backfire barrier 14 is disposed at the second gas outlet 1226, the second communication port 1225, and the first communication port 1223, respectively, so that the filtered gas 1200 and the healthy gas 1228 can be prevented from flowing back. In other embodiments, the backfire barrier 14 may be disposed between the humidifier 120 and the electrolysis device 10 to prevent the gas with hydrogen 106 from flowing back to the electrolysis device 10. It should be understand that although in embodiments of FIG. 2 to FIG. 4 the healthy gas generating system 1 has only one backfire barrier 14 provided at different positions of the gas passage, the number of backfire barrier 14 is not limited thereto. In other embodiments, the healthy gas generating system 1 may install a plurality of backfire barriers 14 at different locations of the gas passages respectively, so that the healthy gas 1228, the filtered gas 1200, and the gas with hydrogen 106 will not flow back. As a result, the gas flow in the healthy gas generating system 1 demonstrates only one-way direction.

In other embodiments, the user may also select the composition of the output gas by controlling the mixing cup 1221 and the vibrator 1222. In detail, turning on the vibrator 1222 will cause the mixing cup 1221 to produce the atomized gas 1227. The atomized gas 1227 will be mixed with the filtered gas 1200 and the healthy gas 1228 will be outputted. In the other case, when the vibrator 1222 is turned off and the mixed cup 1221 does not produce the atomized gas 1227, only the filtered gas 1200 is outputted. In conclusion, the mixing cup 1221 and the vibrator 1222 may selectively output either the healthy gas 1228 or the filtered gas 1200 by the user's selection of turning on or off the vibrator.

Figure 5:
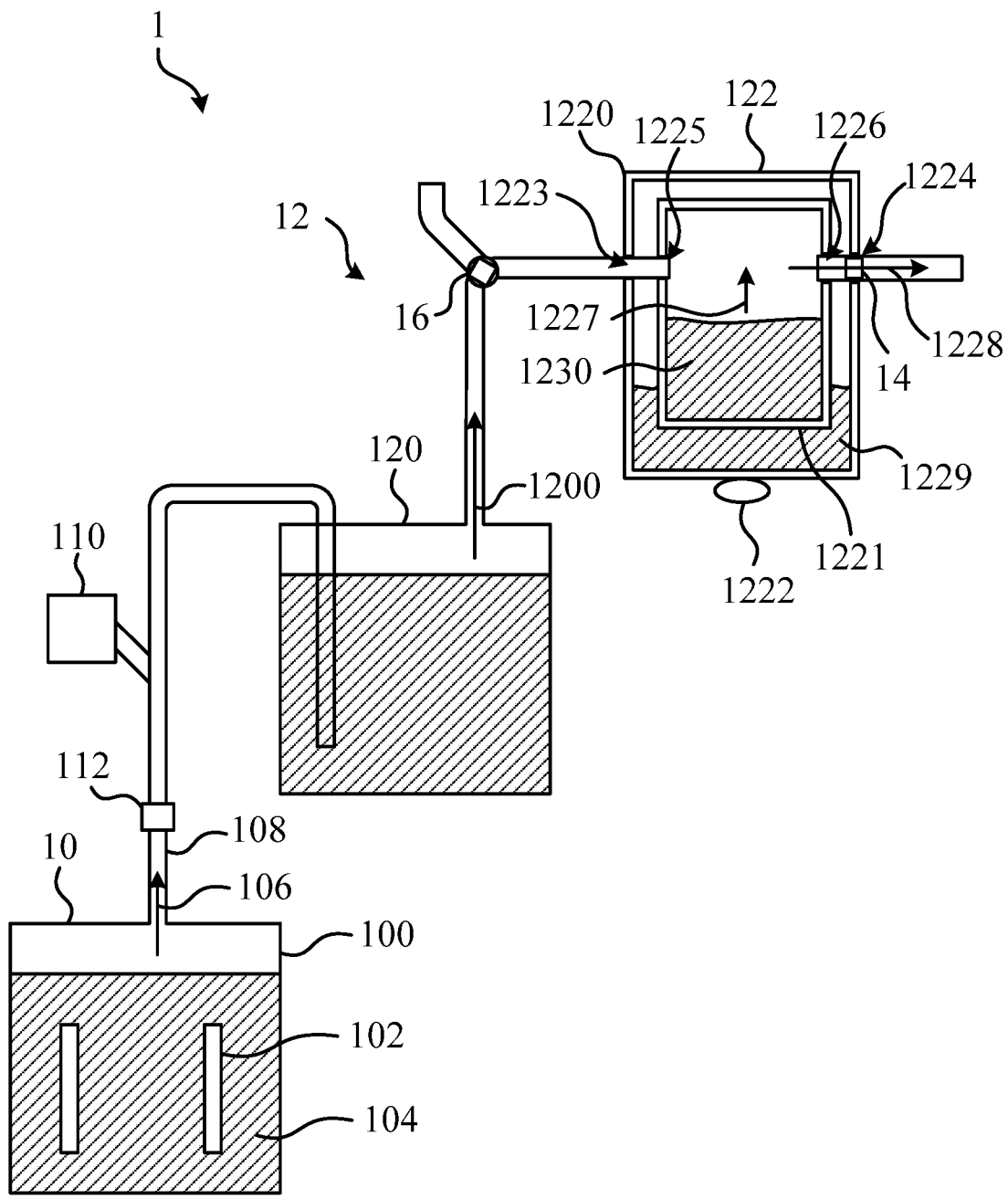
FIG. 5 shows a schematic diagram of the healthy gas generating system in another embodiment of the present invention.

Please refer to FIG. 5. FIG. 5 shows a schematic diagram of the healthy gas generating system 1 in another embodiment of the present invention. As shown in FIG. 5, this particular embodiment differs from the embodiment shown in FIG. 1 in that the healthy gas generating system 1 further comprising a diversion valve 16 configured between the humidifier 120 and the gas mixing tank 122. The diversion valve 16 can be selectively connected to the humidifier 120 and the gas mixing tank 122. Thus, in one case, the filtered gas 1200 with hydrogen is mixed with the atomized gas 1227 and the healthy gas 1228 will be outputted. In the other case, when the diversion valve 16 is switched to the other direction, the filtered gas 1200 does not pass through the gas mixing tank 122 but directly outputs the filtered gas 1200 to the outside for inhalation by a user.

In conclusion, the present invention healthy gas generating system utilizes the backfire barriers to avoid the backflow of the gas and prevent the damage of the healthy gas generating system from an explosion. Thus, the present invention healthy gas generating system of an explosion-proof effect can produce healthy gas with hydrogen whose the volume ratio of the hydrogen may be 2% or less, between 2% and 96% or more. In this way, the healthy gas generation system can freely adjust the hydrogen content by the user's demand, thereby increasing the use of the healthy gas generation system.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A healthy gas generating system, for generating healthy gas to a user to breathe, comprising:
    an electrolysis device for electrolyzing water to generate gas with hydrogen;
    a gas mixing device coupled to the electrolysis device, comprising:
        a shell;
        a gas mixing tank accommodated by the shell, wherein the shell further comprises a first communication port coupled to the electrolysis device;
        a humidifier coupled to the electrolysis device and the gas mixing tank, the humidifier being between the electrolysis device and the gas mixing tank, and configured to contain water to receive and filter the gas with hydrogen;
        wherein the gas mixing tank receives the filtered gas with hydrogen via the first communication port, and the gas mixing tank mixes the filtered gas with hydrogen with an atomized gas to generate a healthy gas and outputs the healthy gas via a first gas outlet; and
    a first backfire barrier positioned before the gas mixing tank and coupled to and in contact with the first communication port of the shell, such that the healthy gas will not flow back to the humidifier; and
    a second backfire barrier positioned between the humidifier and the electrolysis device, such that the gas with hydrogen will not flow back to the electrolysis device.

2. The healthy gas generating system of claim 1, wherein a volume ratio of the hydrogen in the healthy gas generated by the gas mixing device is between 2% to 96%.

3. The healthy gas generating system of claim 1, wherein a volume ratio of the hydrogen in the healthy gas generated by the gas mixing device is more than 96%.

4. The healthy gas generating system of claim 1, further comprising a diversion valve configured between the humidifier and the gas mixing tank, wherein the diversion valve can be selectively coupled to the humidifier and the gas mixing tank, so that the filtered gas with hydrogen is selectively mixed with the atomized gas to generate the healthy gas or output directly.

5. The healthy gas generating system of claim 1, wherein the first backfire barrier is formed with the shell by the method of injection molding, for allowing the first backfire barrier and the shell to be formed in one piece.

6. The healthy gas generating system of claim 1, wherein the shell accommodates a shock base liquid, and the gas mixing tank further comprises:
    a mixing cup, configured in the shell and partially soaked in the shock base liquid, wherein the mixing cup further comprises a second communication port and a second gas outlet, the second communication port is coupled to the humidifier and the first communication port, and the second gas outlet is configured to output the healthy gas, the mixing cup accommodates a liquid, wherein the liquid comprises at least one of essential oil, syrup and pure water; and
    a vibrator configured on the shell, wherein the vibrator shakes the liquid in the mixing cup via the shock base liquid to generate the atomized gas.

7. The healthy gas generating system of claim 6, wherein the gas mixing device selectively outputs the gas through the user selecting the turning on or off the vibrator.

8. The healthy gas generating system of claim 1, further comprising a flow controller, wherein the flow controller is coupled to the electrolysis device to detect a flow rate of the gas with hydrogen, and the detected flow rate controls the production of the gas with hydrogen in the electrolysis device.

9. The healthy gas generating system of claim 8, wherein the flow controller selectively cuts an input voltage or an input current of the electrolysis device according to the flow rate.

10. The healthy gas generating system of claim 1, further comprising an adding gas unit configured between the electrolysis device and the gas mixing device for adding a gas into the gas with hydrogen to reduce a volume ratio of the hydrogen, wherein the gas comprises at least one of air, water vapor, blunt gas and oxygen.

11. The healthy gas generating system of claim 1, wherein the electrolysis device comprises two electrodes electrically coupled to a power supply, and the output voltage of the power supply is less than 24V.

* * * * *